US008506906B2

(12) United States Patent
Griss et al.

(10) Patent No.: US 8,506,906 B2
(45) Date of Patent: Aug. 13, 2013

(54) MICROFLUIDIC DEVICE

(75) Inventors: Patrick Griss, Otelfingen (CH); Björn Samel, Lindingo (SE); Goran Stemme, Stockholm (SE); Frédéric Neftel, Lausanne (CH); Laurent-Dominique Piveteau, Bussigny (CH)

(73) Assignees: Bonsens S.A., Stockholm (SE); Patrick Griss, Otelfingen (CH); Bjorn Samel, Lidingo (SE)

( * ) Notice: Subject to any disclaimer, the term of this patent is extended or adjusted under 35 U.S.C. 154(b) by 805 days.

(21) Appl. No.: 12/092,446

(22) PCT Filed: Nov. 24, 2006

(86) PCT No.: PCT/IB2006/054433
§ 371 (c)(1),
(2), (4) Date: Oct. 1, 2008

(87) PCT Pub. No.: WO2007/060636
PCT Pub. Date: May 31, 2007

(65) Prior Publication Data
US 2009/0044875 A1 Feb. 19, 2009

(30) Foreign Application Priority Data
Nov. 25, 2005 (EP) .................................. 05111343

(51) Int. Cl.
*B81B 7/00* (2006.01)
(52) U.S. Cl.
USPC ........................... 422/503; 137/828; 422/502

(58) Field of Classification Search
USPC .................................. 422/502–505; 137/828
See application file for complete search history.

(56) References Cited

U.S. PATENT DOCUMENTS 6,167,910 B1 * 1/2001 Chow ............................ 137/827
6,273,687 B1    8/2001 Nogimori et al.
6,821,819 B1 * 11/2004 Benavides et al. ............ 438/122
(Continued)

FOREIGN PATENT DOCUMENTS

DE    198 12 436          9/1999
DE    198 12 436 A1       9/1999
(Continued)

OTHER PUBLICATIONS

International Search Report for PCT/IB2006/054433 mailed Jun. 1, 2007.

(Continued)

*Primary Examiner* — In Suk Bullock
*Assistant Examiner* — Paul Hyun
(74) *Attorney, Agent, or Firm* — Nixon & Vanderhye P.C.

(57) ABSTRACT

A microfluidic system comprises a first portion and a second portion. The first portion comprises a material which is able to change its volume when activated by an exciting factor, characterized by the fact that the first portion and the second portion define a zone which, when the first portion is not yet activated by the exciting factor, shows a first topography devoid of any fluidic pathway and which, after activation by the exciting factor, shows a second topography which is adapted to contain at least one fluidic pathway. The microfluidic system further comprises a tight cover surface situated above the first portion and the second portion.

43 Claims, 8 Drawing Sheets

(56) References Cited

U.S. PATENT DOCUMENTS

| | | | |
|---|---|---|---|
| 2001/0049148 A1* | 12/2001 | Wolk et al. | 436/180 |
| 2002/0166585 A1* | 11/2002 | O'Connor et al. | 137/87.01 |
| 2002/0176804 A1 | 11/2002 | Strand et al. | |
| 2003/0156991 A1 | 8/2003 | Halas et al. | |
| 2003/0175947 A1 | 9/2003 | Liu et al. | |
| 2004/0050705 A1* | 3/2004 | Tseng et al. | 204/600 |
| 2004/0094733 A1 | 5/2004 | Hower et al. | |
| 2005/0244308 A1 | 11/2005 | Tanaami et al. | |
| 2005/0274423 A1 | 12/2005 | Oka et al. | |
| 2006/0029808 A1* | 2/2006 | Zhai et al. | 428/412 |

FOREIGN PATENT DOCUMENTS

| | | |
|---|---|---|
| DE | 19812436 | 9/1999 |
| DE | 101 57 317 | 6/2003 |
| DE | 101 57 317 A1 | 6/2003 |
| DE | 10157317 | 6/2003 |
| EP | 1 065 378 A2 | 1/2001 |
| EP | 1 065 378 A2 | 9/2001 |
| EP | 1 700 632 A2 | 9/2006 |
| GB | 2 400 158 | 10/2004 |
| JP | 2002-036196 | 2/2002 |
| JP | 2002-505439 | 2/2002 |
| JP | 2002-066999 | 3/2002 |
| JP | 2003-503716 | 1/2003 |
| JP | 2003-107094 | 4/2003 |
| JP | 2003-139660 | 5/2003 |
| JP | 2004-291187 | 10/2004 |
| JP | 2005-246203 | 9/2005 |
| JP | 2005-257695 | 9/2005 |
| WO | 99/24744 | 5/1999 |
| WO | WO 03/081052 | 10/2003 |
| WO | WO 2004/039500 A1 | 5/2004 |
| WO | WO 2004/113735 A1 * | 12/2004 |
| WO | WO 2005/036182 | 4/2005 |
| WO | WO 2007/064404 A2 | 6/2007 |

OTHER PUBLICATIONS

Written Opinion for PCT/IB2006/054433 mailed Jun. 1, 2007.
International Preliminary Report on Patentability for PCT/IB2006/054433 Mar. 17, 2008.
Samel et al., "Expandable microspheres incorporated in a pdms matrix: a novel thermal composite actuator for liquid handling in microfluidic applications", *Transducers, Solid-State Sensors, Actuators and Microsystems Conference*, vol. 2, Jun. 2003, pp. 1558-1561, XP010647522.
Griss et al., ", Liquid handling using expandable microspheres", *Annual International Conference on Microelectro Mechanical Systems*, vol. 15, Jan. 2002, pp. 117-120, XP010577609.
Andersson et al., "Expandable microspheres-surface immobilization techniques", *Sensors and Actuators B*, vol. 84, No. 2-3, May 2002, pp. 290-295, XP004360403.
Chinese Office Action dated May 12, 2010 and its English Translation from Application No. 200680044136.6.
European Office Action dated Aug. 5, 2011 issued in European Patent Application No. 06 831 933.4.
Japanese Office Action dated Jan. 31, 2012 and its English translation.
European Office Action dated Aug. 5, 2011.

* cited by examiner

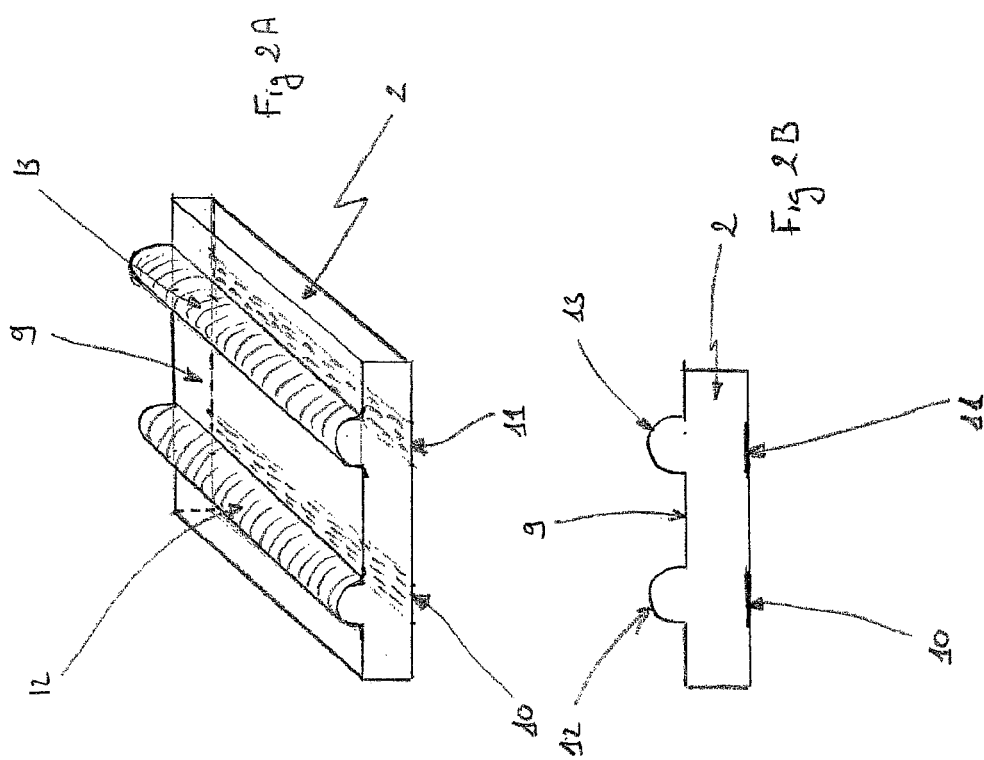
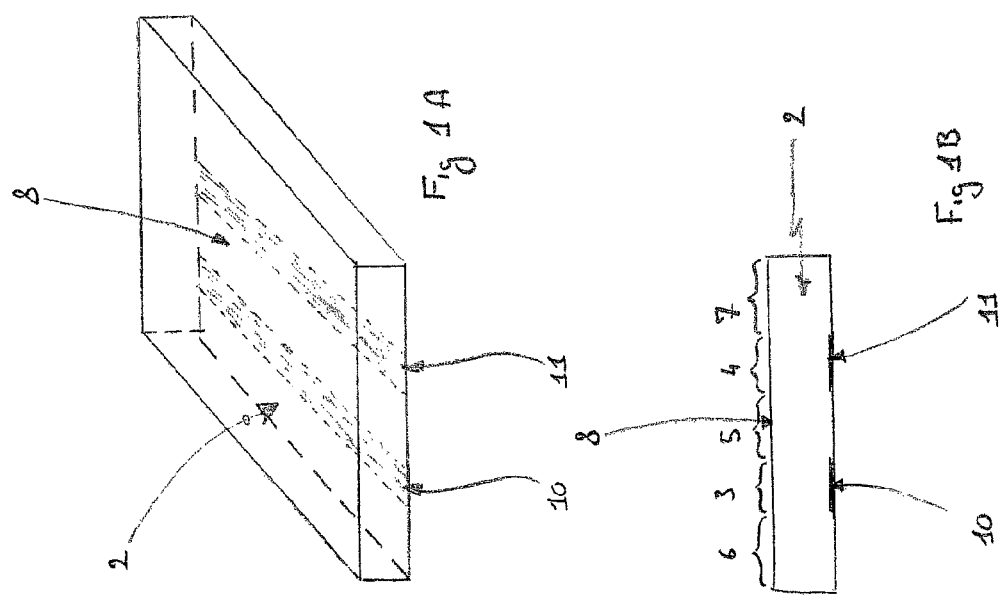

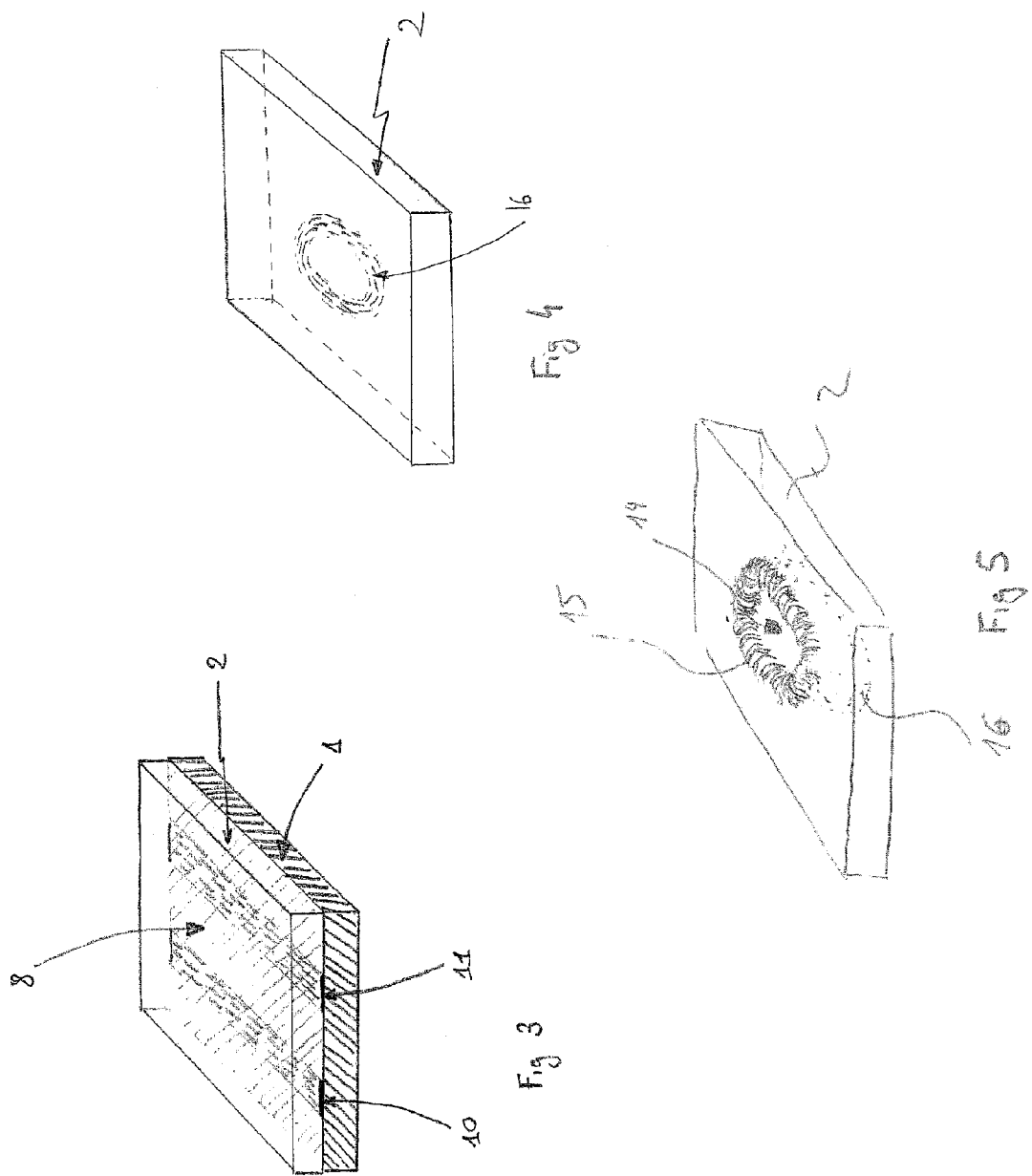

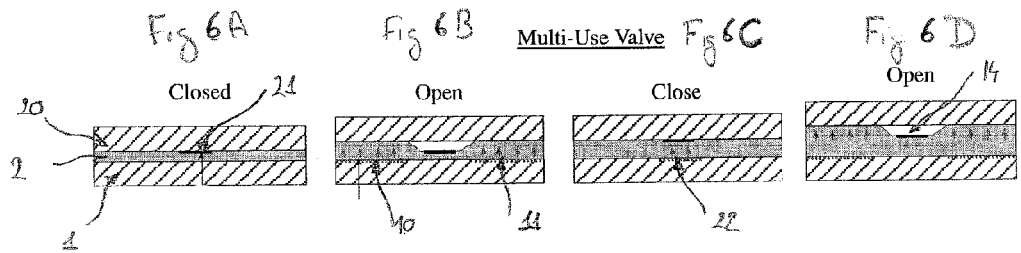
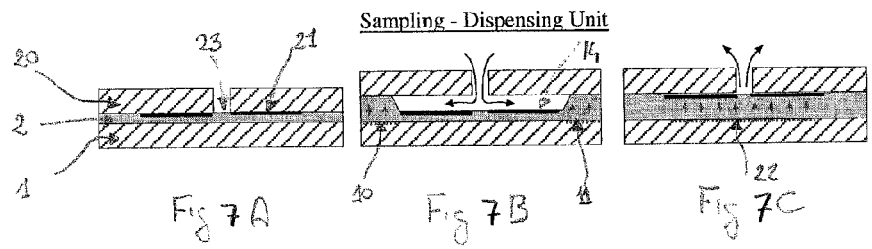
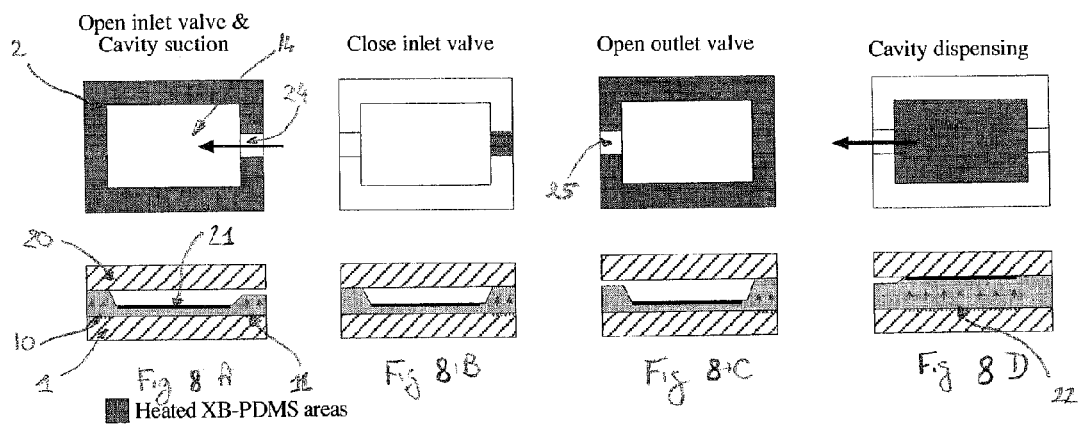
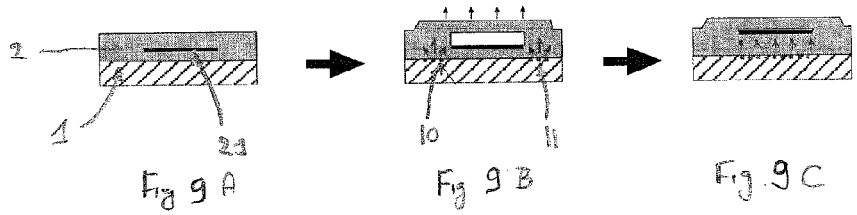
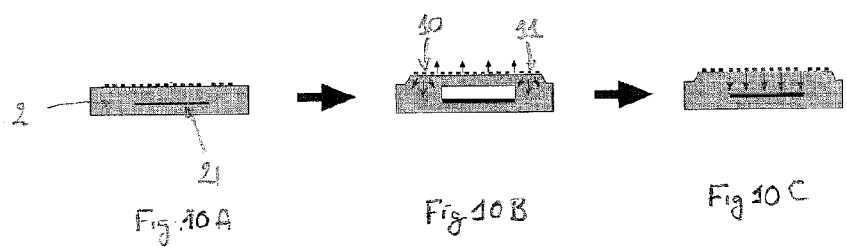

Bimorph Actuator Dispensor Unit
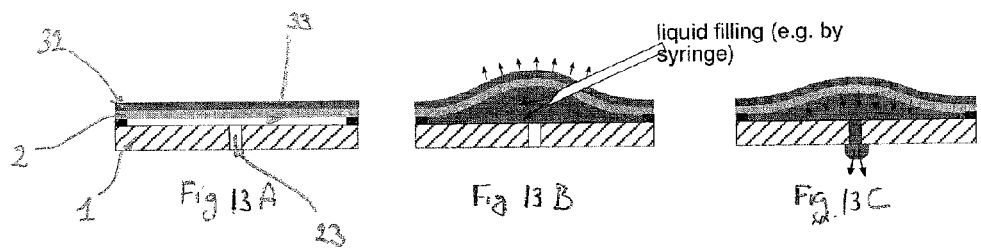
Double Bimorph Actuator Dispensor Unit
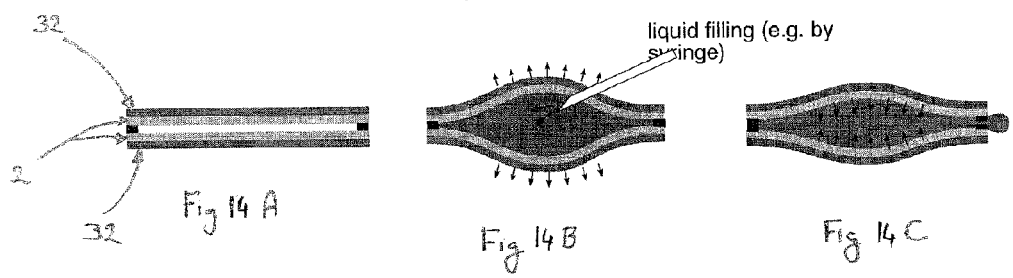
Double Bimorph Suction Dispensor Unit
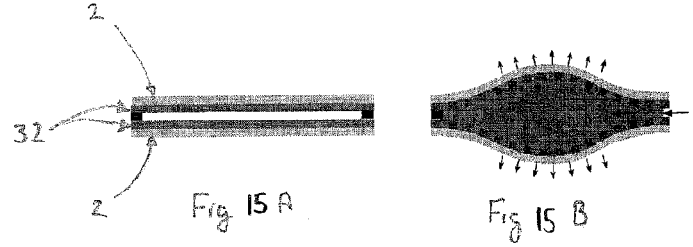
Controlled suction unit
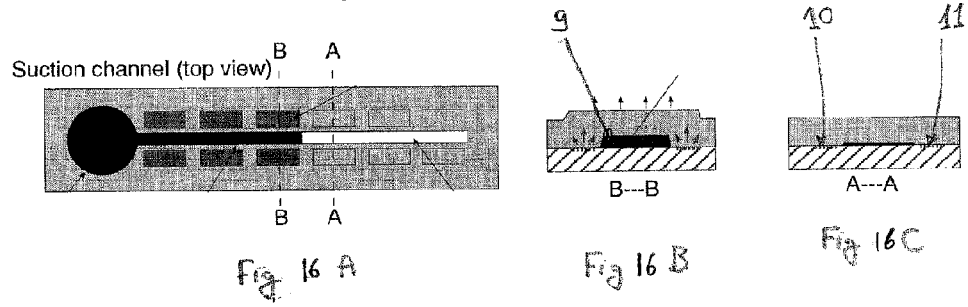

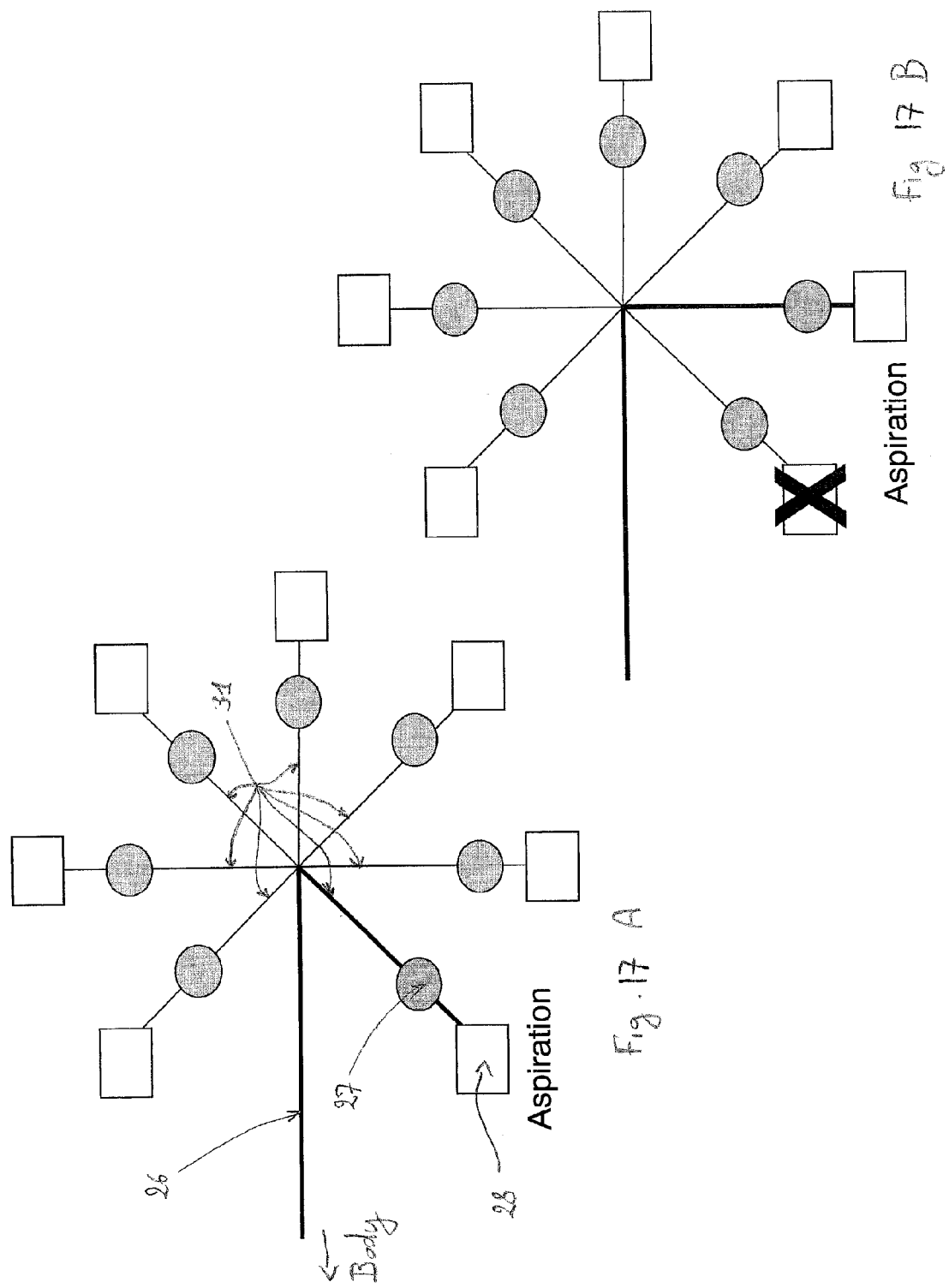

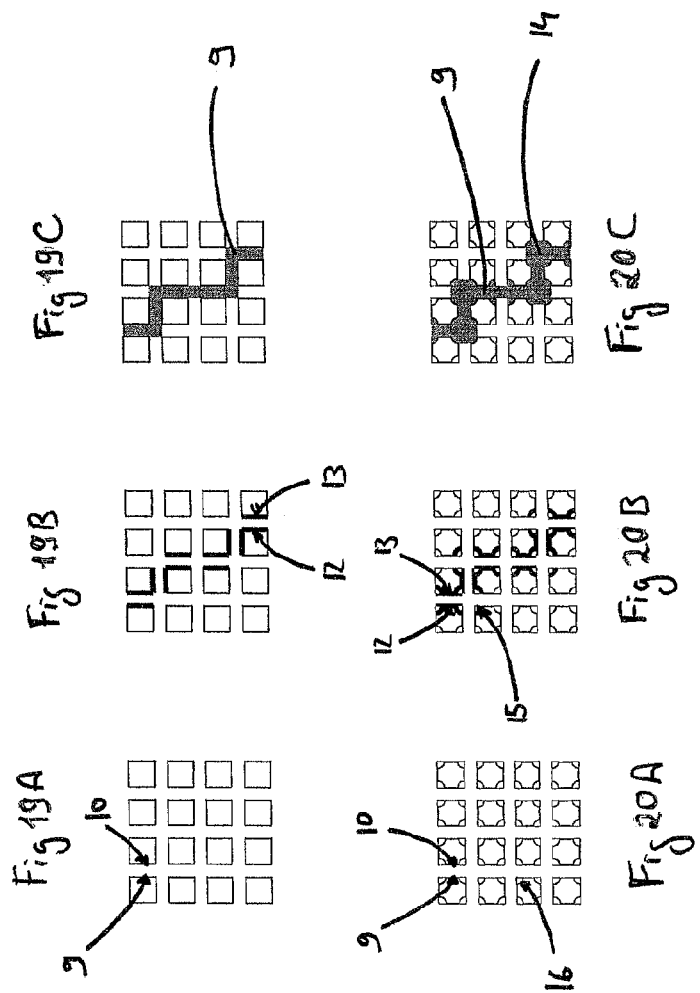

MICROFLUIDIC DEVICE

This application is the U.S. national phase of International Application No. PCT/IB2006/054433 filed 24 Nov. 2006 which designated the U.S. and claims priority to European Patent Application No. 05111343.9 filed 25 Nov. 2005, the entire contents of each of which are hereby incorporated by reference.

FIELD OF INVENTION

The invention relates to microfluidic systems comprising a material which is able to change its volume when activated by an exciting factor. It more precisely relates to such systems which can be used in the medical field as diagnostic or therapeutic devices.

STATE OF THE ART

The development of microfluidic systems has recently grown increasingly attractive and is evolving rapidly. In particular, they offer attractive features such as dramatic reduction in liquid sample consumption since only small volumes are required. This increases sensitivity, speed of analysis, facilitates portable lab-on-chip systems and opens new opportunities for drug delivery devices. Such systems require the integration of various components such as pumps, valves, mixers, separation units, reactors and detectors within a single microfluidic chip. New actuation principles and materials with the advantages of low cost, easy fabrication, easy integration, high reliability, and compact size are desirable and promote the development of sophisticated microfluidic systems. One of these actuation principles, the pushing liquids by closing predefined cavities, has already been described elsewhere. It may be classified into two major types of approaches.

A first approach uses thermopneumatic materials. As the thermopneumatic material is heated, it expands in volume and causes movement of the flexible material forming the cavity, i.e. it causes mechanical movement and therefore closes the cavity. As the thermopneumatic material cools, it returns to its original volume and the flexible material of the capsule returns to its original position accordingly.

In a similar approach, the thermopneumatic material is replaced by a wax undergoing a reversible change in plasticity when heated. Increasing the volume of the wax allows closing predefined cavities.

These approaches have been described into the following patents

"Macromechanical components" WO 03/081052 A1
"Microfluidic substrate assembly and method for making same" US 2002/0176804 A1
"Micro fluidic thermally responsive valve" GB 2 400 158 A Another approach uses Expancel beads dispersed into a PDMS matrix. Heating this mixture causes the irreversible expansion of the Expancel beads, and therefore of the mixture Expancel-PDMS. As a consequence, predefined cavities containing liquids are closed, pumping their content into the microfluidic device. This technology has been described in the following articles:

B. Samel, P. Griss, G. Stemme, "Expandable microspheres incorporated in a PDMS matrix: a novel thermal composite actuator for liquid handling in microfluidic applications", Transducers '03, 1558-1561 (2003).

B. Samel, V. Nock, A. Russom, P. Griss, G. Stemme, "Nanoliter liquid handling on a low cost disposable with embedded fluid actuators", Abstract Transducers '05, EA 1233 (2005).

B. Samel, J. Melin, P. Griss, G. Stemme, "Single use microfluidic pumps and valves base don a thermally responsive PDMS composite", Proceedings MEMS 2005, (2005).

N. Roxhed, B. Samel, L. Nordquist, P. Griss, G. Stemme, "Compact, seamless integration of active dosing and actuation with microneedles for transdermal drug delivery", Abstract MEMS 2006, 0341 (2006).

GENERAL DESCRIPTION OF THE INVENTION

The invention essentially refers to a microfluidic system comprising a first portion and a second portion, said first portion comprising a material which is able to change its volume when activated by an exciting factor, characterized by the fact that said first portion and said second portion define a zone which, when said first portion is not yet activated by said exciting factor, shows a first topography devoid of any fluidic pathway and which, after activation by said exciting factor, shows a second topography which is adapted to contain at least one fluidic pathway, said microfluidic system furthermore comprising a tight cover surface situated above said first portion and said second portion. Compared to the state of the art, this technology allows a very flexible and cheap fabrication of micro-channels, micro-valves and micro-cavities.

The system according to the invention is obtained by using a material that expands or contracts under an external stimulation, whereby volumetric changes are obtained within such material by which channels can be created or closed, valves can be open or close and/or fluid can be pumped in or out.

Materials and General Principle of Functioning

The material used to reach the objective of this invention has to changes in volume when externally stimulated. In one embodiment this material is a mixture of at least two materials. In a preferred embodiment these two materials are polymers. In a preferred embodiment the external stimulation is heat or light. The description below will concentrate, for sake of simplicity, on embodiments made of polymers with heat as external stimulation, but it may obviously be extended to any other type of materials.

An example of commercially available polymer that changes in volume when heat is applied is Expancel®. Expancel® beads are made of a polymeric shell containing a small amount of a liquid hydrocarbon. When heated, the polymeric shell softens while the hydrocarbon becomes gaseous and increases its volume resulting in a dramatic increase of the volume of the beads. Up to a certain temperature that can be adjusted, the beads will increase in size, reaching up to 60 times their starting volume, which corresponds to a multiplication by a factor of four of the bead diameter. All this process is irreversible and can be accomplished in several distinct steps as the size increase is, non-linearly, proportional to the heating temperature. Of course, one can also conceive the same invention by using another material displaying similar properties or even another material which would decrease in size as a result of a given external stimulation The elastic polymer is selected according to its mechanical and chemical properties. It will be chosen among materials with adapted elastic properties and good chemical stability and, in certain cases, biocompatibility. In a preferred embodiment PDMS (polydimethylsiloxane also called silicone) is used. PMDS is especially interesting as it is already used in the medical field. However it may be replaced by any other material with adapted properties.

The mixture can be modified by adding additional elements. For example, salt can be added to reduce the activation temperature for Expancel, or refractive materials can be added to limit heat diffusion and therefore offer a better control of the spatial diffusion of the stimulation leading to expansion or contraction of the material.

In one embodiment, structures are created by locally heating the mixture. In a preferred embodiment, the control of the topography of created structures is obtained by the design of the heating system. Resistors will be disposed directly in contact with the mixture or will be first deposited onto a substrate. The design will reproduce, directly or indirectly, the different cavities, valves and/or channels that will be subsequently opened and possibly closed.

Creating Cavities and Channels

The creation of cavities is done by locally heating the mixture and therefore creating walls. The height of the walls is defined by the stimulation applied during the heating and therefore the extent of expansion of the expandable material. The ceiling of the cavities can be obtained by covering the mixture with a surface that can be either made of the same material or of another material. To avoid adhesion between the bottom and the ceiling an anti-adhesive layer is introduce in-between. In a preferred embodiment the anti-adhesive layer is made of gold.

Depending on the shape of the heating resistor, different type of cavities can be created. An example is show in FIGS. 1 and 2 where the cavity is a channel. Another example is given in FIGS. 4 and 5 where the cavity has a circular shape, resulting in a disk. Resistors can also be disposed in a repetitive way as shown in a possible embodiment in FIGS. 20 and 21 creating a type of matrix structure. Depending on the need of the user, resistors can be activated creating customized types of channels and cavity topographies.

Opening of cavities can be used, for example, to pump in liquid. The suction force can be either induced by the negative pressure induced by the opening of the cavity, or by an external force used to push the liquid from the inlet, or by a combination of both.

Closing Cavities and Channels

Cavities, valves and/or channels can then be closed by specific stimulation (heating) of material areas which expansion will fill the cavity or channel.

This sequence and opening and closing can be repeated several times. This is done by only partially expanding the Expancel beads, as described above.

DETAILED DESCRIPTION OF THE INVENTION

The invention will be better understood hereafter in a detailed description including the following figures:

FIGS. 1A and B show the device before its activation. In this embodiment, heating resistances of linear shape (10&11) underlie said first part (3 &4). They define a region (8) that will become after activation a channel.

FIGS. 2A and B show the same device after activation. Walls have grown (12 & 13) that define a hollow region (9) having the form of a channel FIG. 3 shows another embodiment where a passive substrate (1) is added.

FIG. 4 shows and embodiment where the activation system (16) has a loop shape.

FIG. 5 shows the same embodiment as FIG. 4 after activation.

FIGS. 6A to D show the functioning of a possible embodiment for a multi-use valve. FIG. 6A shows the mixture layer sandwiched between two surfaces. In FIG. 6B, the said first part is activated creating a cavity (14). In FIG. 6C the cavity is closed by activating the bottom of the cavity. FIG. 6D shows how the cavity can be re-opened by activating again the same parts as in FIG. 6B.

FIGS. 7A to C show the functioning of a possible embodiment for a sampling and dispensing unit. FIG. 7A shows the mixture layer sandwiched between two surfaces, one having a through hole (23). In FIG. 7B a cavity (14) is created, provoking a depression that will suck in liquid through the hole. By closing the cavity (FIG. 7C) the liquid is ejected from the cavity.

FIGS. 8A to D show the functioning of a possible embodiment for a lateral suction and dispensing unit. In FIG. 8A, the cavity is created by growing walls except for some space to create an inlet (24). Liquid is sucked into the cavity (14) by the created depression. The inlet is then closed (FIG. 8B) and an outlet (25) created (FIG. 8C) by a process similar to the one used to create the cavity. The cavity is then closed by activating its bottom and, as a consequence, the liquid is ejected.

FIGS. 9A to C show another embodiment for a multi-use valve where the mixture is deposited on a substrate and the cavity is opened into the mixture.

Figure 11:
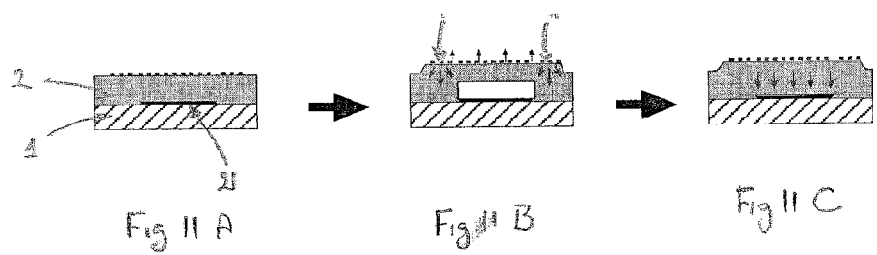
Figure 12:
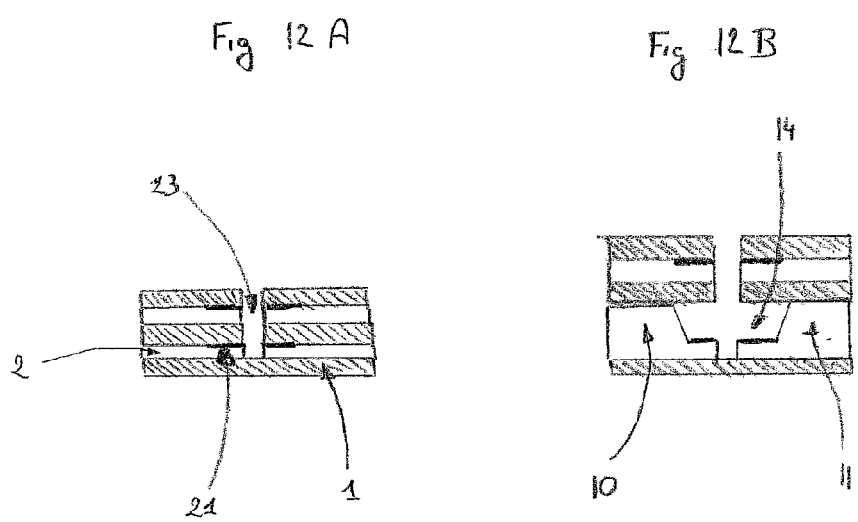
Figure 12:
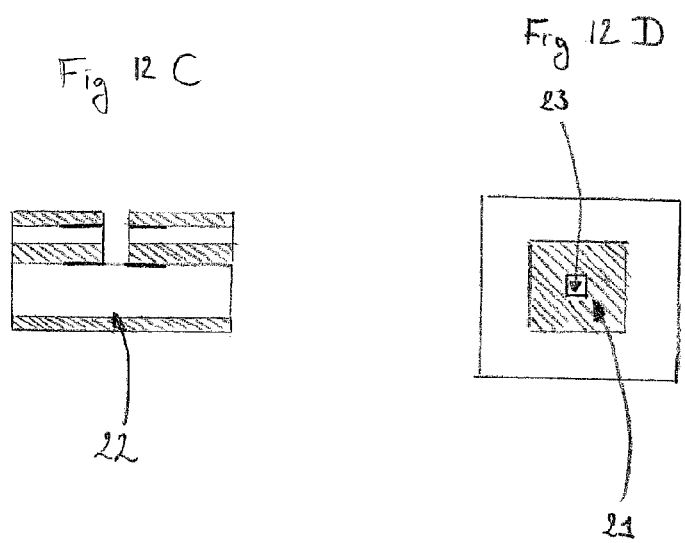
Figure 18:
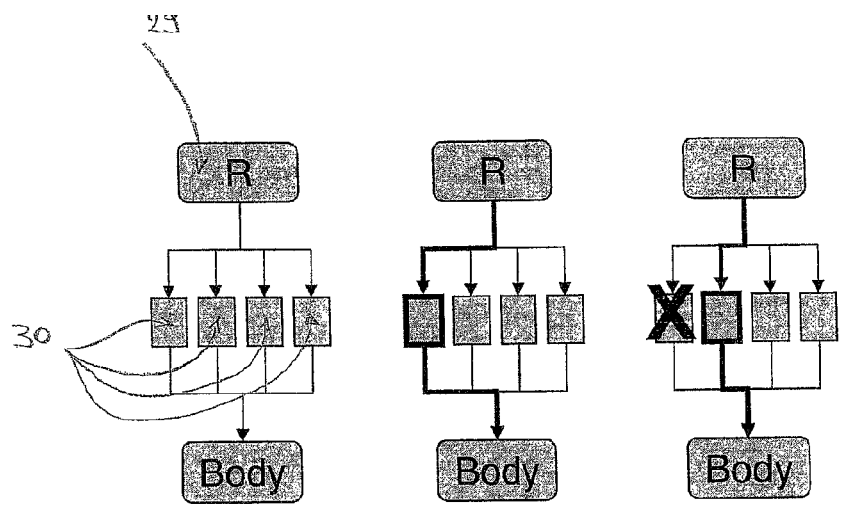
Figure 18:
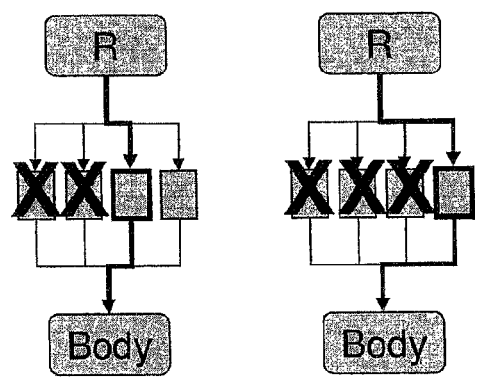

FIGS. 10A to C show another embodiment for a multi-use valve where no substrate is present and where the cavity is created into the mixture FIGS. 11A to C show another embodiment for a multi-use valve where the mixture is deposited onto a substrate and the cavity is opened at the interface between the substrate and the mixture.

FIGS. 12A to D show another embodiment for sampling and dispensing units as well as its functioning. Here several units are piled up together and activated one after another. The different working steps are shown for the lower unit, but can be repeated for each upper unit.

FIGS. 13A to C show another embodiment for the invention where the mixture is combined with a flex-PCB (32) to form a bi-layer. They are deposited onto a hard substrate with a through hole (23), leaving an empty volume in-between (33). It acts as a suction bi-morph actuator.

FIGS. 14A to C show another embodiment where two bi-layers are joined together. The flex-PCB side is on the outside. It acts as a suction bi-morph actuator.

FIGS. 15A to B show another embodiment where two bi-layers are joined together. The flex-PCB side is on the outside. It acts as a dispenser bi-morph actuator.

FIGS. 16A to C show another embodiment for a controlled suction device. In this case the liquid is progressively driven into a channel that is open by lateral heating systems.

FIGS. 17A and B show a possible embodiment for a multiple diagnosis device. In this embodiment the liquid of interest is sucked into a cavity with detection device through the depression created by the opening of another cavity. The disposition of several diagnosis cavities into a rose like shape allows several sequential measurements using a single aspiration line.

FIGS. 18A to E show a possible embodiment for a single reservoir multi injection system. A series of lateral and suction and dispensing units are connected to the same reservoir. By using them in a sequential way, it is possible to make several injections of the same amount of liquid through a single injection line.

FIG. 19 A to C show a possible embodiment of a device offering the possibility of customizing micro-channels. FIG. 19 A shows the disposition of heating resistors. In FIG. 19 B a series of resistors, selected by the final user, are activated. They provoke the extension of the mixture and create a fluidic path as shown in FIG. 19 C.

FIG. 20 A to C show a similar embodiment to that show in FIG. 20 where cavities and channels are combined.

The following numerical references are used in the text below:
1. Basis wafer
2. Expandable element
3. Left active portion
4. Right active portion
5. Middle passive portion
6. Left passive portion
7. Right passive portion
8. Surface
9. Channel
10. Left heating element
11. Right heating element
12. Left flange
13. Right flange
14. Cavity
15. Annular flange
16. Annular heating element
17. —
18. —
19. —
20. Cover wafer
21. Anti-adhesion layer
22. Middle heating element
23. Central upper passage
24. Inlet valve
25. Outlet valve
26. Single open channel
27. Preformed cavity
28. Aspiration cavity
29. Drug reservoir
30. Lateral suction and dispensing unit
31. Flower structure
32. PCB-Expancel-PDMS bi-layer
33. Non-bonded region Multi-Use Pumping Volume and Valve In a first embodiment, the mixture layer is sandwiched between a basis wafer (1) and a cover wafer (1, 20). An anti-adhesion layer (21) is deposited on top of the mixture in contact with the upper plate as shown in FIG. 6A. By using heating elements (10, 11) placed onto the bottom plate the mixture is locally grown to create a cavity (14) (FIG. 6B). This cavity is then closed by again locally heating (22) the mixture (FIG. 6C) in front of the cavity. By repeating this process the valve can be opened and closed several times (FIG. 6D) until the material has been expanded to its limit.

Sampling and Dispensing Unit

In another embodiment, the cover wafer (20) is drilled with a through hole (23) allowing liquid to flow in and out of the created cavity (14) (FIG. 7A). During the first heating period, the liquid is sucked into the cavity by a differential pressure effect (FIG. 7B). It is then re-ejected when the centre part of the cavity is expanded (FIG. 7C). This device can be used over several cycles until the material has been expanded to its limit.

Multiple Sampling and Dispensing Units

In another embodiment, several sampling and dispensing units can be piled up. In a first stage, the lower sampling and dispensing unit is used. It is opened by heating the walls and then closed again by heating the floor. In following stages, the different sampling and dispensing units are used, going from the bottom to the top. For each cycle, as can be seen on FIG. 12, the liquid enters and leaves the cavity through the same hole.

Lateral Suction and Dispensing Unit

In another embodiment, a cavity is created by heating the walls except for a small portion that will act as an inlet valve (24). Liquid enters the cavity either sucked by the depression created by the opening of the cavity of pushed from the outside (FIG. 8A) through the inlet. In a second step (FIG. 8B) the inlet is closed. In a third step (FIG. 8C) walls are grown again except for a small portion that will act as an outlet valve (25). The cavity is eventually closed (FIG. 8D) by heating its bottom, ejecting, as a consequence, the stored liquid through the outlet.

Controlled Suction Unit

In another embodiment, the liquid is sucked into a channel that is progressively opened. At the beginning, the liquid is stored into a reservoir. By heating resistors (10, 11) placed along the channel (FIG. 16C) a channel (9) is progressively formed (FIG. 16B). The liquid contained into the reservoir is therefore progressively sucked into the formed channel by the negative pressure induced by its formation (FIG. 16A) or as a result of a positive pressure applied on the fluid reservoir at the inlet.

Diagnostic Device Based on a Flower Like Structure

In another embodiment (FIG. 17A), a liquid is sucked from the body through a single channel (26). It is then distributed through a flower like structure (31) into preformed cavities (27) where a diagnostic device is placed. Aspiration into the cavity is done by the opening of another cavity (28) situated after the cavity on the fluidic path that creates a depression into the system. Several measurements can be conducted with the same device using each time a new routing into a blank diagnosis cavity (27) for the liquid (FIG. 17B). Such a system can be used, as an example, for glucose measurement at given time intervals, each such measurement being done with a new sensor situated within a new cavity. Such a system can be interestingly coupled to a micro-needle array onto the patient's skin in order to obtain interstitial fluid at each measurement time, either on patient demand (directly on the device or by a remote wireless device) or automatically based on predetermined intervals managed by a microprocessor.

In a similar embodiment the aspiration cavity can be the diagnosis cavity. It is created and opened to suck up the liquid to be analysed. In another embodiment, the cavity may suck up in addition to the liquid to be analyzed other reagents located in other cavities that are progressively closed.

Injection Device with a Single Reservoir and Multiple Suction and Dispensing Units In another embodiment (FIG. 18A), a single reservoir (29) containing a liquid of interest is connecting several lateral suction and dispensing cavities (30) which are themselves connected to the body through a single line. By opening a first suction and dispensing cavity (FIG. 18B), a controlled amount of liquid is retrieved from the reservoir and, by closing such cavity, a fixed amount is injected into the body. By placing several of these units in parallel, multiple injections of a controlled volume from a single reservoir can be conducted (FIG. 18B to E). Programmable amounts of drug can therefore be injected, based on volume of cavities created by using such induced stimulation of the expandable or retractable material.

In the event of using a retractable material, all prior applications can be made by inverting the process between walls and cavity.

Channels Closing Laterally

In another embodiment, channels are created into the mixture. After their opening, a liquid is inserted into this microfluidic path. It is then pushed, in a peristaltic or progressive way, into this path by the lateral closing of the channel. This lateral closing is obtained by heating the walls of the channel.

In another embodiment, the effect of the lateral closing is increased by preventing the vertical expansion of the walls when heated.

Bimorph Actuator Dispensing or Suction Unit

In another series of embodiments, the mixture is combined with a flexible PCB to form a bimorph. In a bimorph actuator two thin panels of ceramic elements are bonded together with a flexible metallic panel. By elongating one of the ceramic elements, inflection deviation occurs in the normal direction, on the side of the non-elongating ceramic. In these embodiments, one of the ceramic elements, the expending one, is replace by the Expancel-PDMS mixture, while the other ceramic element and the flexible metallic panel are combined together under the form of a flexible PCB. These are bond together to form a bi-layer with bimorph behaviour.

By heating the mixture, elongation will occur generating a normal force to the PCB-Expancel—PDMS bi-layer (32). The displacement occurs in the normal direction, on the side of the flexible PCB. In a first embodiment, the bi-layer is connected to a basis wafer leaving a non bonded region (33) in between (FIG. 13 A). The Expancel-PDMS layer is placed on the outside. A liquid is then inserted into this cavity, deforming the bi-layer (FIG. 13 B). By heating the Expancel-PDMS layer of the bi-layer, expansion occurs creating a force towards the interior of the cavity (normal direction on the side of the non-expanding material). This force induces a displacement of the bi-layer and the closing of the cavity. The liquid is ejected through a hole into the basis wafer (FIG. 13 C).

In another embodiment, the basis wafer is replaced by another bi-layer. The functioning principle is similar to the former embodiment. A liquid is inserted into the cavity and, after expansion of the Expancel-PDMS layer, rejected through a predefined opening (FIGS. 14 A to C). In this embodiment, however, the cavity may contain more liquid. Effectively, when the liquid is inserted into the cavity, the cavity size will increase along the normal axis while reducing its dimensions into the plane defined by the two bi-layers, forming a pillow like structure. This geometry is more favourable than that with a hard basis wafer inducing (for the same external surface, it has more volume).

In another embodiment, the two bi-layers are connected together with the Expancel-PDMS mixture on the inside of the cavity. When the mixture is heated, a normal force appears and displacement occurs towards the outside. A liquid can therefore be suck into the created cavity (FIGS. 15 A and B)

Permanent Heating—Disposable Mixture

In another embodiment, the heating system can be a permanent part and be re-used several times while the Expancel-PDMS mixture is a disposable part that is replaced between each use. The heating system can comprise the electronic part as well as batteries to supply power.

In a preferred embodiment, this approach is used for drug delivery patches. A disposable part containing the drug of interest is combined with a permanent part containing the heating system and the power supply. On a regular basis, the disposable part is replaced by a new one.

In a preferred embodiment, it is combined with a system favouring the opening of micro-channels into the skin. These micro-channels are known to facilitate the transport of a drug through the stratum corneum, the protective layer of the skin.

In a preferred embodiment, these micro-channels are created by micro-needles.

Use of Flexible Batteries

In another embodiment, the Expancel-PDMS mixture can be deposited onto a flexible battery. This battery will act as the power supply for the heating system and become an integrant part of the final device.

Creation of Channels and/or Cavities Network

In another embodiment, channels and cavities can be custom designed. Channels and cavities can be opened in advance or can be drawn by the final user.

In a preferred embodiment, resistors are disposed in a repetitive way as shown FIGS. 19 and 20 creating a type of matrix structure. Depending on the need of the user, resistors can be activated creating customized types of channels and cavity topographies.

In a preferred embodiment, a laser is used to draw the channels and the cavities in the mixture. When scanning the surface, the laser locally heats the Expancel-PDMS mixture, provoking its expansion and therefore creating channels and cavities. In the same way, the laser can be used to close the channels and the cavities and push the liquid that is inside.

In another embodiment, biocompatibility of the device is increase by introducing a biocompatible layer into the fluidic path. It is located between the mixture Expancel-PDMS and the liquid of interest. The liquid of interest is therefore isolated for the PDMS, reducing risks of incompatibility. This layer may act as the anti-bonding layer

The invention claimed is:

1. A microfluidic system comprising:
   a first portion, and
   a second portion,
   said first portion comprising a material which is able to change its volume when activated by an exciting factor, wherein said first portion and said second portion define a zone which, when said first portion is not yet activated by said exciting factor, the zone shows a first topography devoid of any fluidic pathway and which, after activation by said exciting factor, the zone shows a second topography which defines at least one fluidic pathway,
   said microfluidic system further comprising a tight cover surface situated above said first portion and said second portion, and
   wherein said first and second portions are deposited on a basis surface.

2. The microfluidic system according to claim 1 wherein said material is adapted to be activated by heat or light as exciting factor.

3. The microfluidic system according to claim 1 wherein said material, when activated, remains in the same configuration.

4. The microfluidic system according to claim 1 wherein said second topography includes a channel.

5. The microfluidic system according to claim 1 wherein said second topography includes a cavity.

6. The microfluidic system according to claim 1 wherein said second portion is made of a material which is able to change its volume when activated by an exciting factor.

7. The microfluidic system according to claim 6 wherein said first portion and second portion both comprise the same material.

8. The microfluidic system according to claim 1 wherein said material is expandable.

9. The microfluidic system according to claim 1 wherein said material is collapsible.

10. The microfluidic system according to claim 1 comprising an anti-adhesion layer which is situated between the second portion and the cover surface.

11. The microfluidic system according to claim 6 wherein said second portion is designed to be an active portion.

12. The microfluidic system according to claim 11 wherein said first portion and said second portion are adapted to alternately expand multiple times sequentially creating thereby a multi-dose delivery device.

13. The microfluidic system according to claim 12 wherein said cover surface comprises a central passage.

14. Method of using a microfluidic system according to claim 11, comprising activating the active portions, said activation resulting in the creation of a fluidic pathway.

15. Method according to claim 14 wherein the creation of a fluidic pathway induces a fluid aspiration in the system.

16. Method according to claim 14 wherein the creation of a fluidic pathway is characterized by successive increases and decreases of the fluidic pathway.

17. Method according to claim 14 wherein the microfluidic system acts as a dose collecting device.

18. The microfluidic system according to claim 1 comprising an inlet valve and/or an outlet valve, said valve(s) comprising said material.

19. The microfluidic system according to claim 1 comprising heating elements situated close to said first and second portions.

20. The microfluidic system according to claim 1 wherein said material is expandable and is a mixture comprising beads made of a polymeric shell containing a liquid hydrocarbon.

21. The microfluidic system according to claim 1 wherein said material is expandable and is a mixture comprising PDMS or a biocompatible material.

22. The microfluidic system according to claim 1 forming a multilayered structure comprising successive surfaces and expandable elements connected by at least one common passage.

23. The microfluidic system according to claim 1 wherein said system is formed by screen printing.

24. The microfluidic system according to claim 1 wherein said system is formed by molding of the material.

25. The microfluidic system according to claim 1 designed in such a way that the material is expandable and is adapted to expand in the second topography along a lateral direction.

26. The microfluidic system according to claim 25 wherein the material is designed to progressively expand along a wall of the second topography creating thereby a progressive fluid movement.

27. The microfluidic system according to claim 1 wherein said material comprises a heat diffusion preventing material in order to better limit heat diffusion.

28. The microfluidic system according to claim 1 combined with a programmable heating system.

29. The microfluidic system according to claim 1 combined with one or several external reservoirs.

30. The microfluidic system according to claim 1 combined with micro needles.

31. The microfluidic system according to claim 1 combined with at least one fluid content detection means.

32. The microfluidic c system according to claim 1 combined with a feed-back system adapted to regulate the deformation of the material and/or the volume expelled.

33. The microfluidic system according to claim 1 including a film type battery.

34. An assembly comprising the microfluidic system according to claim 1, said assembly comprising a cavity in front of the zone, said cavity being adapted to contain a fluid to be analysed by a sensor.

35. Assembly comprising several microfluidic systems according to claim 1, each microfluidic system communicating with a single inlet element and each second topography, wherein a sensor is connected to the inlet element.

36. Assembly comprising several microfluidic systems according to claim 1, said assembly comprising a central reservoir communicating with each second topography.

37. An assembly comprising several microfluidic systems according to claim 1, wherein said assembly is a matrix type assembly.

38. Combination of a single-use microfluidic system according to claim 1 with a reusable heating system.

39. Method of using a microfluidic system according to claim 1, comprising activating said material by heat.

40. Method according to claim 39 wherein heat is generated by an electric resistance, infrared light or laser.

41. Method according to claim 39 wherein the volume or flow of liquid in the microfluidic system is determined by the control of heat quantity.

42. A microfluidic system comprising:
a first portion, and
a second portion,
said first portion comprising a material which is able to change its volume when activated by an exciting factor, wherein said first portion and said second portion define a zone which, when said first portion is not yet activated by said exciting factor, the zone shows a first topography devoid of any fluidic pathway and which, after activation by said exciting factor, the zone shows a second topography which defines at least one fluidic pathway,
said microfluidic system further comprising a tight cover surface situated above said first portion and said second portion, and
wherein said material is expandable and is a mixture comprising beads made of a polymeric shell containing a liquid hydrocarbon.

43. A microfluidic system comprising:
a first portion, and
a second portion,
said first portion comprising a material which is able to change its volume when activated by an exciting factor, wherein said first portion and said second portion define a zone which, when said first portion is not yet activated by said exciting factor, the zone shows a first topography devoid of any fluidic pathway and which, after activation by said exciting factor, the zone shows a second topography which defines at least one fluidic pathway,
said microfluidic system further comprising a tight cover surface situated above said first portion and said second portion, and
wherein said material comprises a heat diffusion preventing material in order to better limit heat diffusion.

* * * * *